United States Patent [19]

Tagami

[11] Patent Number: 5,170,775
[45] Date of Patent: Dec. 15, 1992

[54] ENDOSCOPE
[75] Inventor: Satoshi Tagami, Tama, Japan
[73] Assignee: Olympus Optical Co., Ltd., Tokyo, Japan
[21] Appl. No.: 700,226
[22] Filed: May 14, 1991
[30] Foreign Application Priority Data
  Jun. 20, 1990 [JP] Japan .................. 2-163918
[51] Int. Cl.⁵ .............................................. A61B 1/00
[52] U.S. Cl. ........................................ 128/4; 358/98
[58] Field of Search ................... 128/4, 6; 358/98
[56] References Cited

U.S. PATENT DOCUMENTS

| 3,190,286 | 6/1965 | Stokes | 358/98 |
|---|---|---|---|
| 4,301,323 | 9/1982 | Ouchi et al. | 128/4 |
| 4,700,693 | 10/1987 | Lis et al. | 128/4 |
| 4,777,524 | 10/1988 | Nakajima et al. | 128/4 |
| 4,899,787 | 2/1990 | Ouchi et al. | 128/4 |
| 4,944,727 | 7/1990 | McCoy | 128/4 |
| 4,971,033 | 11/1990 | Ehlers | 128/4 |
| 4,974,580 | 12/1990 | Anapliotis | 128/4 |
| 5,014,515 | 5/1991 | Krouter | 128/4 |
| 5,035,231 | 7/1991 | Hubokawa et al. | 128/4 |

FOREIGN PATENT DOCUMENTS 1-24501  5/1989  Japan .
1-90019  6/1989  Japan .

Primary Examiner—Paul J. Hirsch
Attorney, Agent, or Firm—Armstrong & Kubovcik

[57] ABSTRACT

In an endoscope of this invention, an electroconductive member is exposed in at least a part of an insertable section to be inserted into an inspected object in which either pole of a battery is earthed and, in the course leading from the electroconductive member exposed in the insertable section to an external apparatus, an insulating member electrically insulating the electroconductive member and external apparatus is provided.

18 Claims, 12 Drawing Sheets

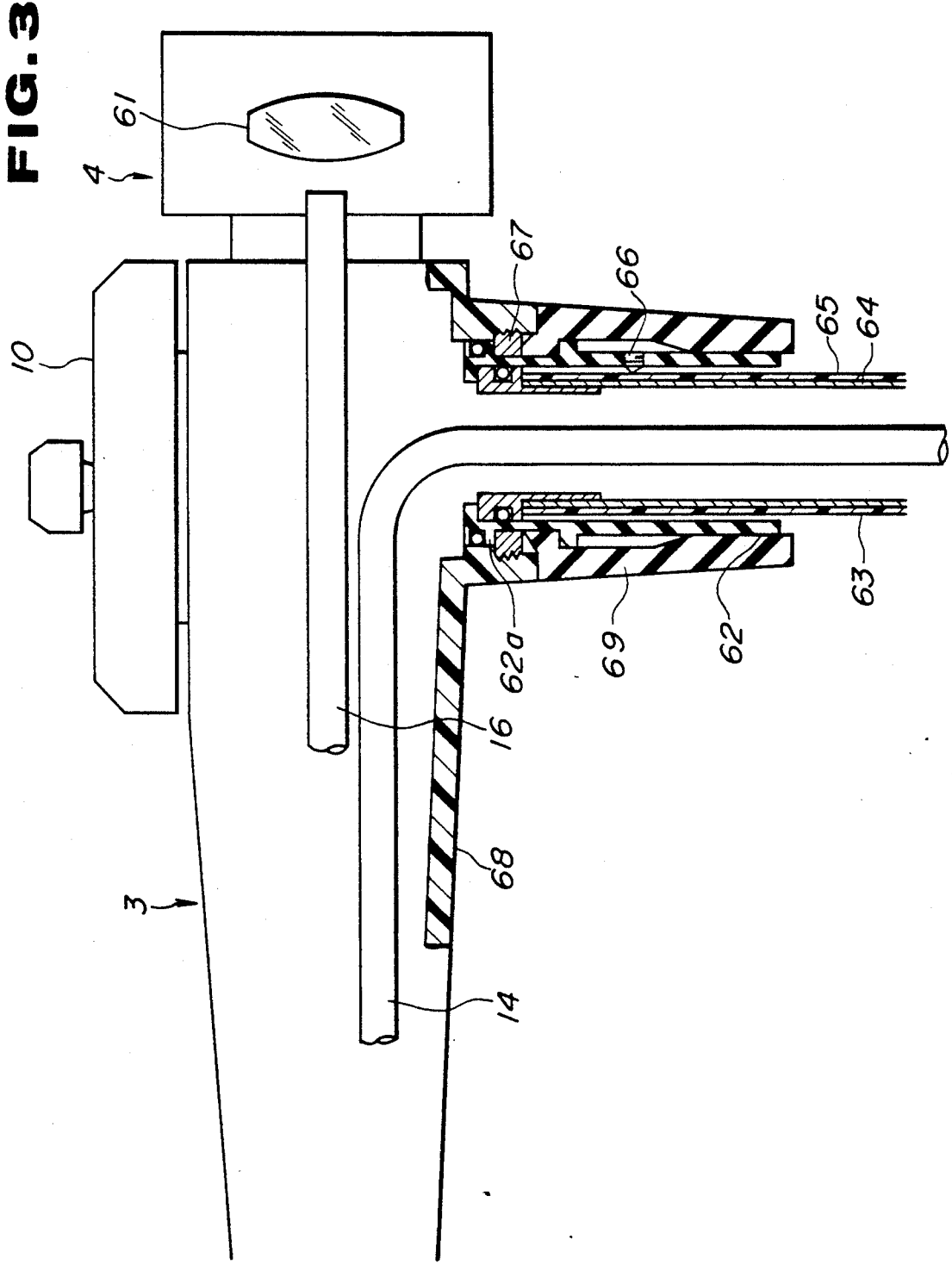

ENDOSCOPE

BACKGROUND OF THE INVENTION

1. Field of the Invention

This invention relates to an endoscope adapted to inspect an object in which either pole of a battery is earthed.

2. Related Art Statement

Recently, industrial endoscopes are extensively utilized to observe and inspect flaws and corrosions within pipings of boilers, gas turbine engines and chemical plants and bodies of automobile engines.

Now, such industrial endoscope has, for example, an elongate insertable section, an operating section provided at the rear end of this insertable section and a light guide cable extended from this operating section and is to be connected to a light source apparatus through a connector provided at the rear end of this light guide cable.

The above mentioned insertable section is formed, for example, of a rigid tip part, a curvable part and a flexible part in the order from the tip side. The members forming the above mentioned insertable section and light guide cable are mostly of a metal and metal parts are often exposed.

A light source apparatus to which this industrial endoscope is connected is earthed. Therefore, as in an automobile or the like, in case one pole of a battery is earthed to the chassis and various electric articles are connected to the other pole of the battery, when such exposed metallic part as of the above mentioned insertable section touches the pole of the battery on the side to which the electric article is connected, an electric current will flow within the endoscope through the metal parts of the insertable section and light guide cable, will destroy an endoscope or such external apparatus as a light source apparatus forming endoscope apparatus, will hurt a car body with a spark, will destroy an electric article and will be further likely to give an electric shock to the operator and observer.

In order to cope with it, in the publication of Japanese Utility Model Application Laid Open No. 162186 1979 is disclosed an endoscope of a structure wherein a jointing member jointing a hardware part tip part of an endoscope tip part and curvable tube part curvable part or a jointing member jointing a curvable tube part and flexible tube part soft part is coated on the outer surface with such insulating layer as of a rubber lining to develop a water leakage preventing function and outer coating insulating function.

However, in the technique shown in the above mentioned publication, in order to insulate the interior of the endoscope so that no electric current may flow, it is a prerequisite that the hardware part of the endoscope tip part and the curvable tube part should be insulatively coated on the outer periphery. That is to say, in case these are not insulatively coated, when they touch the pole of the battery, an electric current will be likely to flow through the insulatively coated jointing member or the metal part inside it.

Now, with the industrial endoscope to be used to inspect or repair an automobile engine or body, as different from the medical endoscope to be used to inspect such object as a human body, an object in which many metal parts are used is inspected and therefore a special consideration for keeping a durability on the outer periphery of the industrial endoscope is necessary. Particularly, in the endoscope tip part and curvable tube part, it may be advantageous to leave the metal as it is on the outer periphery or it may be necessary to secure the durability by coating the metal blade net tube.

Therefore, in the technique shown in the above mentioned publication, it is necessary that the hardware part of the endoscope tip part and curvable part should be insulatively coated on the outer periphery with such material as will remain durable enough even in an environment of many metals. However, such material is generally expensive or often will not be able to be kept durable enough in case it is proper in the price.

OBJECTS AND SUMMARY OF THE INVENTION

An object of the present invention is to provide an endoscope wherein the formation is simple and, in the case of observing an inspected object in which either pole of the battery is earthed, even when the insertable section touches the non earthed side of the battery, no electricity will conduct and the endoscope apparatus or inspected object will not be damaged.

Another object of the present invention is to provide an endoscope wherein the formation is simple and, in the case of observing an inspected object in which either pole of the battery is earthed, even when the insertable section touches the non earthed side of the battery, no electricity will conduct and the operator and observer will not be injured.

Briefly, in the endoscope of the present invention, between an exposed electroconductive member in the insertable section and an external apparatus forming the endoscope apparatus is provided an insulating member electrically insulating the electroconductive member and external apparatus.

The other features and advantages of the present invention will become apparent enough with the following explanation.

BRIEF DESCRIPTION OF THE DRAWINGS

FIG. 1 is a sectioned view of the tip side of an insertable section of an endoscope.

FIG. 2 is an explanatory diagram showing a whole endoscope apparatus.

FIG. 3 is a sectioned view showing the vicinity of an operating section of an endoscope in the second embodiment of the present invention.

FIG. 4 is an explanatory view of an endoscope apparatus as being used.

FIG. 5 is a sectioned view of the tip side of an insertable section of an endoscope.

FIG. 10 is an explanatory view showing the connection of an endoscope and signal processing apparatus.

FIG. 11 is a sectioned view of a connector.

FIG. 12 is a general view of an endoscope apparatus.

FIG. 13 is a sectioned view on line A A in FIG. 12.

FIG. 14 is a sectioned view of a light source apparatus.

FIG. 15 is a sectioned view of a lamp holder part of the light source apparatus.

DETAILED DESCRIPTION OF THE PREFERRED EMBODIMENTS

Figure 1:
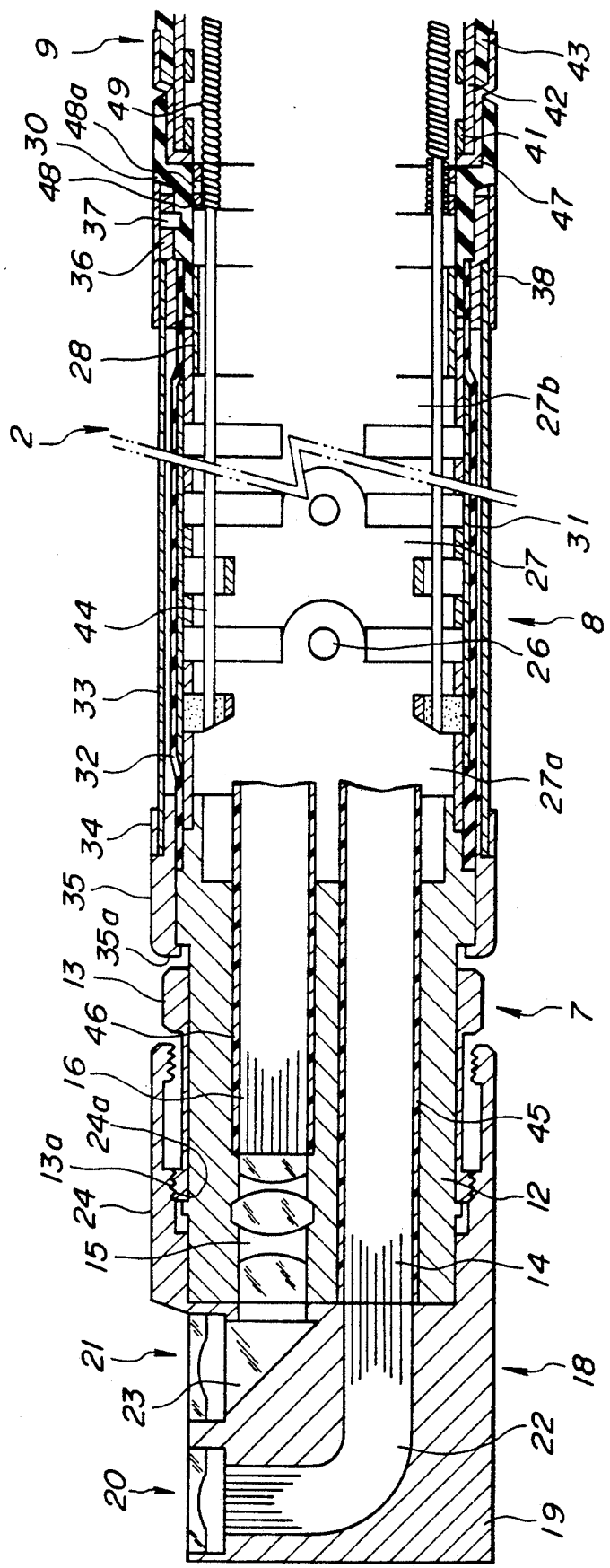
FIGS. 1 and 2 relate to the first embodiment of the present invention.
Figure 2:
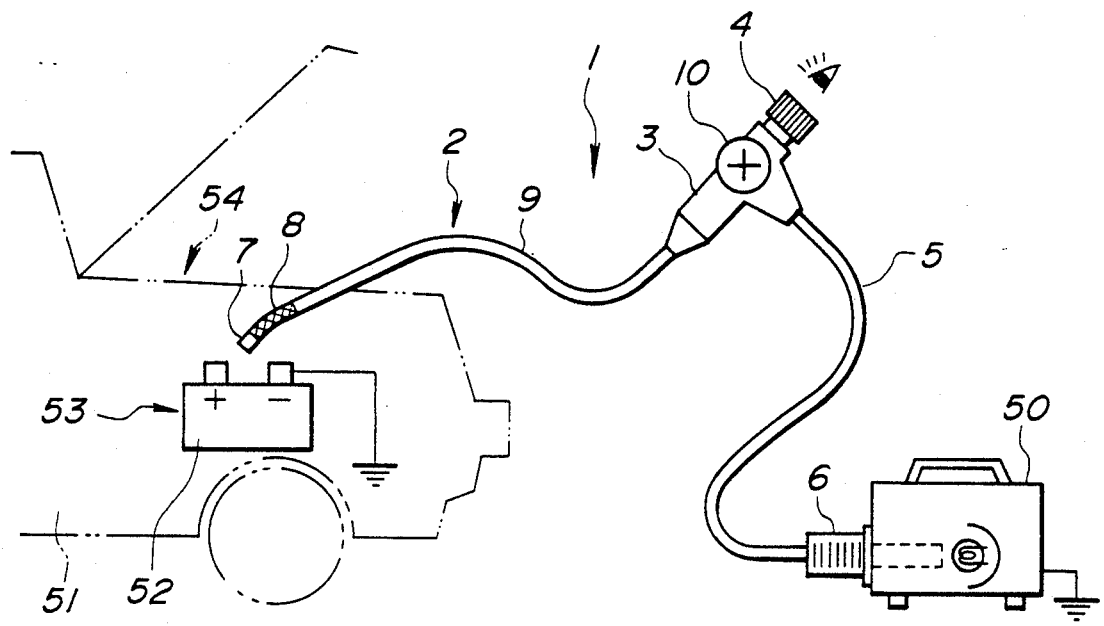

FIGS. 1 and 2 show the first embodiment of the present invention. As shown in FIG. 2, an industrial endoscope apparatus comprises an endoscope 1 and a light source apparatus 50 as an external apparatus connected with this endoscope 1 and forming an endoscope apparatus.

The above mentioned endoscope 1 comprises an elongate insertable section 2, a thick operating section 3 provided at the rear end of this insertable section 2, an eyepiece section 4 provided at the rear end of this operating section, a light guide cable 5 as a connecting cable connected to the above mentioned light source apparatus 50 and a light guide connector 6 provided at the end of this light guide cable 5. The above mentioned light guide connector 6 is removably connected to the above mentioned light source apparatus 50.

The above mentioned insertable section 2 comprises a rigid tip part 7, curvable part 8 and soft part 9 in the order from the tip side. The above mentioned operating section 3 is provided with a curving operation knob 10 for curving the above mentioned curvable part 8 and is formed on the outer surface of such electric insulative material as, for example, plastics so as to be used also as a holding part. The above mentioned light guide cable 5 is covered on the outer surface with such electric insulative material as, for example, plastics.

FIG. 2 shows the above mentioned endoscope apparatus as inspecting the interior of an automobile 51 which is an object to be inspected. A battery apparatus 53 comprising a battery 52 and a distributor and ignition apparatus not illustrated is provided within the above mentioned automobile 51. This battery apparatus 53 is earthed on the minus side to a chassis 54 of the automobile 51. The above mentioned light source apparatus 50 is also earthed.

As shown in FIG. 1, the above mentioned tip part 7 comprises a tip part body 12 made of a metal for securing a strength and an adapter screw 13 made of a metal and rotatably provided on the outer periphery of this tip part body 12. The above mentioned tip part body 12 is provided with an illuminating through hole and observing through hole parallel in the axial direction of the insertable section 2. A light guide 14 made of a fiber bundle of an electric insulative material is inserted and fixed at the tip within the above mentioned illuminating through hole.

This light guide 14 is coated with a protective tube 45 made of silicone, is inserted through the insertable section 2, operating section 3 and light guide cable 5 and is connected at the entrance end to the light guide connector 6. An illuminating light emitted from the above mentioned light source apparatus 50 is radiated to an inspected object position from the tip part 7 through the above mentioned light guide 14.

Within the above mentioned observing through hole, an objective optical system 15 is provided on the tip side and an image guide 16 made of a fiber bundle of an electric insulative material is inserted and fixed on the tip side in the rear of this objective optical system 15. The tip surface of this image guide 16 is arranged in the image forming position of the above mentioned objective optical system 15.

The above mentioned image guide 16 is coated with a protective tube 46 made of silicone and is inserted through the insertable section 2 and operating section 3 and its rear end surface is opposed to an eyepiece optical system not illustrated within the eyepiece section 4. The optical image of the inspected object position formed by the above mentioned objective optical system 15 is led to the eyepiece section 4 by the image guide 16 and is magnified and observed in this eyepiece section 4.

Any optical adapter which can vary the visual field angle and visual field direction can be selectively fitted to the above mentioned tip part body 12. In FIG. 1 is shown an example of a side viewing optical adapter 18. This optical adapter 18 has an adapter body 19 provided on one side with an illuminating window 20 and observing window 21 in the order from the tip side in the axial direction of the insertable section 2.

A light guide 22 optically connecting the above mentioned illuminating window 20 and the tip surface of the light guide 14 within the tip part body 12 and a prism 23 optically connecting the above mentioned observing window 21 and the objective optical system 15 within the tip part body 12 are provided within the adapter body 19.

The above mentioned adapter body 19 is provided on the rear end side with a cylindrical part 24 externally fitted to the outer periphery of the above mentioned tip part body 12. This cylindrical part 24 is provided on the inner periphery with a female screw part 24a and the adapter screw 13 is provided with a male screw part 13a screwed to the above mentioned female screw part 24a. When the cylindrical part 24 is externally fitted to the tip part body 12 and the adapter screw 13 is rotated to screw both screw parts 13a and 24a with each other, the optical adapter 18 will be fixed to the tip par body 12.

The curvable part 8 has a plurality of non electro conductive curvable rings 27 connected in the axial direction of the insertable section 2 rotatably with each other by rivets 26. These curvable rings 27 are made of such engineering plastics as, for example, phenol, polyacetal, polycarbonate or polyphenylene oxide or ceramics. The curvable ring 27a at the foremost end is bonded and fixed to the tip part body 12. The curvable ring 27b at the rearmost end is connected to a connecting member 30 made of such electric insulative material as, for example, plastics through a ring 28.

By the way, the above mentioned curvable rings 27 may be plated or coated with an electric insulative material so as to be non electroconductive.

Further, the above mentioned curvable rings 27 are coated on the outer periphery with a metallic curvable inner blade net tube 31, curvable rubber 32 and metallic curvable outer blade 33 in the order mentioned. The above mentioned inner blade 31 is fixed at the tip to the foremost end curvable ring 27a and at the rear end to the rearmost end curvable ring 27b.

Also, the above mentioned curvable rubber 32 is fixed at the tip to the foremost end curvable ring 27a and tip part body 12 and at the rear end to the above mentioned connecting member 30. To the above mentioned outer blade 33 on the tip side is connected an outer blade mouthpiece 35 by an outer blade fixing ring 34.

This outer blade mouthpiece 35 is provided at the tip with an inward projecting pawl part 35a fixed as engaged with a step part on the outer periphery of the tip part body 12. A retaining member 36 is fixed to the rear end part of the above mentioned outer blade 33 and is fixed to the connecting member 30 by a pin 37. The outer blade 33 fixing part by this pin 37 is provided on the outer periphery with a ring 38.

The soft part 9 comprises a flex 41 made by spirally working a metal plate material, a metal blade 42 and an electric insulative resin tube 43 in the order from the inner peripheral side. These tip parts are bonded and fixed to the rear end side of the above mentioned connecting member 30 through a tip member 47 made of such electric insulative material as plastics.

Also, to the above mentioned connecting member 30 is bonded and fixed a metallic ring 48 to which are brazed coil pipes 49 made by spirally winding metal wires. The above mentioned ring 48 is provided with a small hole 48a in the position in which the above mentioned coil pipes 49 are to be brazed so that, in the brazing work in assembling, the positioning of the above mentioned coil pipes 49 and the brazing amount may be sighted and confirmed.

Further, non electroconductive angle wires 44 made of such electric insulative materials as, for example, stainless steel wires coated with nylon or the above described engineering plastics are inserted through the above mentioned coil pipes 49 and are fixed and connected at the tips to the inner periphery of the foremost curvable ring 27a with a non electroconductive bonding agent or the like.

The above mentioned angle wires 44 inserted through the above mentioned coil pipes 49 are inserted through the insertable section 2 and are connected at the rear ends to a curving mechanism provided within the operating section 3 so that the above mentioned angle wires 44 may be prevented from being entangled within the insertable section 2 and, even when the insertable section is 2 flexed, the curvable performance will be secured.

By the way, in this embodiment, the plurality of curvable rings 27 are connected on the right and left by the rivets 26 so as to be rotatable in the vertical direction. Two of the above mentioned angle wires 44 are provided for curving in the vertical direction and are respectively fixed above and below on the inner periphery of the foremost curvable ring 27a.

In this embodiment, as metal parts are used near the inspected object into which the insertable section 2 is inserted, a physical strength will be required on the tip side of the insertable section 2. Therefore, the outer peripheral parts of the tip part 7 and curvable part 8 of the insertable section are formed of a metal.

On the other hand, the soft part 9 is coated with an electric insulative member resin tube 43. The member forming the curvable part 8 and the member forming the soft part 9 are electrically perfectly insulated by the above mentioned connecting member 30. Further, the outer surface of the path leading to the light source apparatus 50 through the light guide cable 5 from the operating section 3 at the rear end of the above mentioned soft part 9 is covered with such electric insulative material as, for example, plastics.

The light guide 14 and image guide 16 inserted and fixed in the tip part body 12 made of a metal are made of an electric insulative material and are coated respectively with protective tubes 45 and 46 made of silicone, the foremost end curvable ring 27a fixed to the above mentioned tip part body 12 and the angle wires 44 connected to this foremost curvable ring 27a are also non el electroconductive and therefore the electricity will not conduct to the operating section 3 side through the insertable section 2 from the tip part body 12 made of a metal.

In this case, the above mentioned curvable ring 27 may be at least partly non electroconductive and, as the angle wires 44 are connected to the foremost curvable ring 27a through the non electroconductive bonding agent, even if the foremost curvable ring 27a and angle wires 44 are electroconductive, the electricity will not conduct to the operating section 3 side through the insertable section 2 from the tip part body 12 made of a metal.

The operation of this embodiment shall be explained in the following.

The outer surface of the greater part soft part 9 of the insertable section 2 of the endoscope 1 is coated with the electric insulative resin tube 43 and the outer surfaces of the operating section 3 and light guide cable 5 are also covered with the electric insulative material. Therefore, even if these parts simultaneously touch the plus side of the battery apparatus 53 and the chassis 54, the electricity will not conduct between them, will not short to damage the observed object or will not ignite.

On the other hand, though a metal is exposed on the outer surface on the tip side from the curvable part 8, in case the tip side from this curvable part 8 touches the plus side of the battery apparatus 53, as the connecting member 30 is of an electric insulative material, even if the light guide cable 5 connected to the earthed light source apparatus 50 conducts to the earth, the electricity will not conduct through the endoscope 1, will not shock the operator and observer, will not damage the observed object or will not ignite and will be still safe.

As not only the outer surface but also the curvable rings 27, angle wires 44 and their connecting parts are made non electroconductive, the electricity will not conduct through the insertable section 2 and will be safe.

By the way, as the length of the conducting part on the tip side from the curvable part 8 is generally much shorter than the distance between the electrodes of the battery 52, the tip side from the curvable part 8 will not touch both electrodes of the battery 51 and further will not simultaneously touch the plus side of the battery apparatus 53 and the chassis 54.

Thus, according to this embodiment, with a simple formation, the electric safety of the endoscope apparatus is elevated. That is to say, even if the insertable section 2 of the endoscope 1 touches the plus side of the battery apparatus 53, the endoscope 1 will not electrically conduct, therefore no spark will be generated and the endoscope apparatus, chassis 54, electric equipments, operator and observer will not be damaged.

FIG. 3 shows the second embodiment of the present invention. In this embodiment, the connecting member connecting the operating section 3 of the endoscope 1 and the light guide cable 5 is formed of an electric insulative material.

The same as in the first embodiment, the image guide 16 and light guide 14 pass through the operating section 3, the image guide 16 is extended to the eyepiece section 4 and then its rear end surface is opposed to an eyepiece optical system 61 within the eyepiece section 4. A flexible tube 63 forming the light guide cable 5 is connected to the side of the above mentioned operating section 3 through a connecting member 62 and the above mentioned light guide 14 is inserted through this flexible tube 63 and is connected to the light guide connector 6.

The above mentioned flexible tube 63 is formed of a flexible tube 64 made of a metal and a protective tube 65 coating this tube 64 and made of a polyester resin or vinyl chloride resin. The above mentioned connecting member 62 is formed of such electric insulative material as plastics and the above mentioned flexible tube 63 is inserted at the end inside this connecting member 62 and is fixed to the connecting member 62 by a fixing screw 66.

A flange part 62a is provided on the outer periphery of the operating section 3 side of the above mentioned connecting member 62 and the connecting member 62 is fixed to the operating section 3 by screwing a ring like fixing screw 67 in contact with this flange part 62a with a female screw part formed in the body 68 of the operating section 3. This connecting member 62 is coated on the outer periphery with a protective cylindrical rubber 69 and is bonded and fixed. Thus, in this embodiment, the insertable section 3 and light guide cable 5 are electrically perfectly insulated by the connecting member 62.

By the way, in the insertable section 2 in this embodiment, the curvable rings 27, connecting member 30 and angle wires 44 may be or may not be formed of an electric insulative material. The other formations are the same as in the first embodiment.

In this embodiment, even if the metal part on the tip side of the insertable section 2 contacts the plus side or the like of the battery apparatus 53 and the electricity is conducted even into the operating section 3 by the component members made of a metal within the insertable section 2 and operating section 3, as they are insulated by the connecting member 62 connecting the operating section 3 and light guide cable 5, the electricity will not be conducted to the light guide cable 5.

Therefore, with a simple formation, the electric safety of the endoscope apparatus is elevated. That is to say, even if the insertable section 2 of the endoscope 1 contacts the plus side of the battery apparatus 53, the endoscope 1 will not electrically conduct, no spark will be generated and the endoscope apparatus, chassis 54, electric equipments, operator and observer will not be damaged.

By the way, in this embodiment, if the first embodiment is used together, that is, the connecting member 30 connecting the curvable part 8 and soft part 9 is formed of an electric insulative material and the curvable rings 27 and angle wires 44 are made non electroconductive, the electric safety will become higher. The other operations and effects are the same as in the first embodiment.

Figure 5:
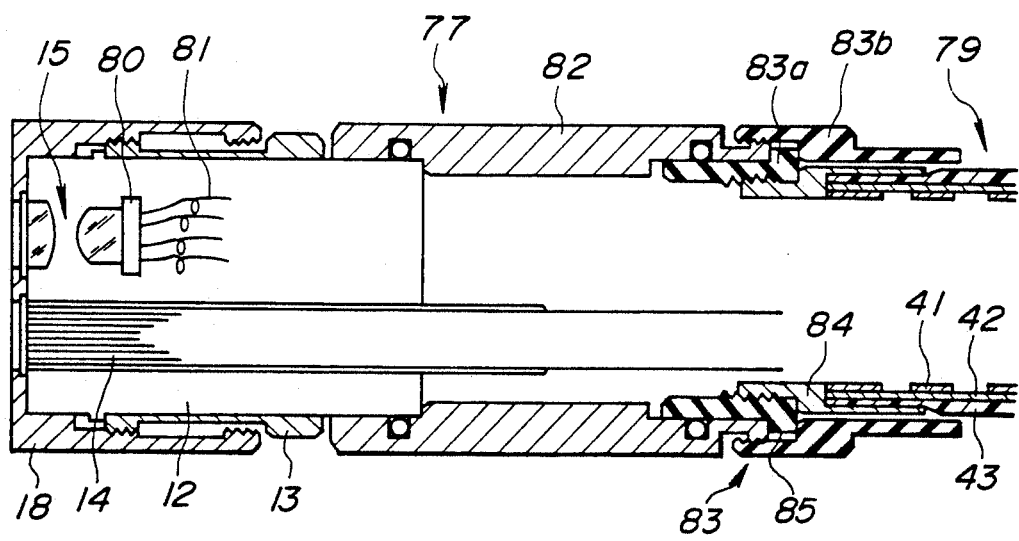
FIGS. 4 and 5 relate to the third embodiment of the present invention.
Figure 4:
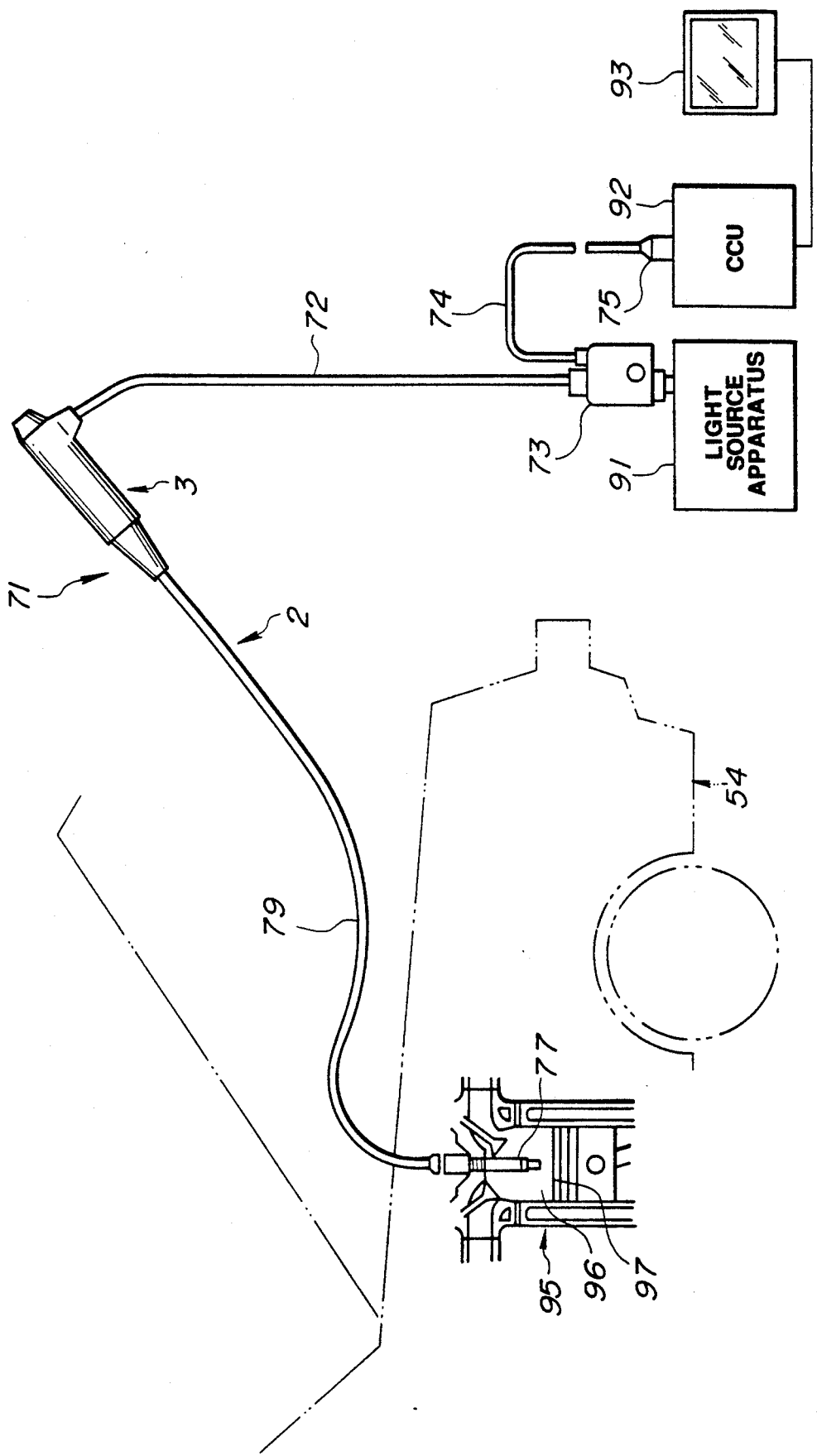

FIGS. 4 and 5 show the third embodiment of the present invention. The endoscope 71 of this embodiment is an electronic endoscope for observing a cylinder 96 of an engine 95.

The endoscope apparatus in this embodiment comprises an endoscope 71, a light source apparatus 91 and camera controlling unit abbreviated as a CCU hereinafter 92 connected with this endoscope 71 and a monitor 93 connected with this CC 92.

The above mentioned endoscope 71 comprises an insertable section 2, an operating section 3 and a universal cord 72 as a connecting cable extended sidewise from this operating section 3. This universal cord 72 is provided at the end with a light source connector 73 removably connected to the above mentioned light source apparatus 91. A cable 74 is extended from the above mentioned light source connector 73 and is provided at the end with a CCU connector 75 removably connected to the above mentioned CCU 92.

The above mentioned insertable section 2 comprises a rigid tip part 77 and a soft part 79 in the order from the tip side but no curvable part. As shown in FIG. 5, the above mentioned tip part 77 has a tip part body 12 made of a metal and this tip part body 12 is provided on the tip surface with an illuminating window and observing window. Inside the above mentioned illuminating window is arranged the tip surface of the light guide 14. This light guide 14 is inserted through the insertable section 2, operating section 3 and universal cord 72 and is connected at the entrance end to the light source connector 73 so that the illuminating light emitted from the light source apparatus 91 may be emitted from the illuminating window through the above mentioned light guide 14.

Inside the above mentioned observing window is provided an objective optical system 15 and such an imaging device as, for example, a charge coupled device abbreviated as a CCD hereinafter 80 is arranged in the image forming position of this objective optical system 15. Signal wires 81 connected to this CCD 80 are inserted through the insertable section 2, operating section 3, universal cord 72, light source connector 73 and cable 74 and are connected to the CCU 92 through the CCU connector 75.

The image of the inspected object position formed by the above mentioned objective optical system 15 is photoelectrically converted by the CCD 80 and the output signal of this CCD 80 is input into the CCU 92 through the signal wires 81 and is processed to be a video signal which is input into the monitor 93 in which the image of the inspected object position is displayed.

By the way, the same as in the first embodiment, the above mentioned tip part body 12 can be fitted with the optical adapter 18.

A cylinder 82 made of a metal is connected to the above mentioned tip part body 12 at the rear end and the soft part 79 is connected to this cylinder 82 at the rear end through a connecting member 83 formed of an electric insulative material. The above mentioned soft part 79 is formed of a flex 41 made by spirally working a metal plate material, a metal blade 42 and an electric insulative resin tube 43 in the order from the inner peripheral side and is connected at the tip to a mouthpiece 84. The above mentioned connecting member 83 is formed of two bodies of an inner tube part 83a and outer tube part 83b.

The above mentioned mouthpiece 84 is screwed to the inner peripheral part of the above mentioned inner tube part 83a which is internally fitted to the cylinder 82 at the rear end. A flange part 85 formed on the rear end side of the inner tube part 83a is in contact with the cylinder 82 at the rear end.

On the other hand, the above mentioned outer tube part 83b has a step on the inner periphery and is screwed to the outer periphery of the rear end part of the cylinder 82 to hold the flange part 85 of the above mentioned inner tube part 83a with this step and the rear end part of the cylinder 82. Thus, in this embodiment, the tip part 77 and soft part 79 are electrically perfectly insulated by the connecting member 83.

In this embodiment, as shown in FIG. 4, the tip part 77 is inserted into the cylinder 96 from an ignition plug hole and the inside wall of this cylinder 96 and a piston head 97 are observed with the endoscope apparatus.

The insertable section 2 is protected in the part to be inserted into the cylinder 96 with a metal part for securing the durability. However, even if the wiring of the electric system of the ignition plug or the like contacts the engine 95 or tip part 77, due to the connecting member 83, the tip part 77 and operating section 3 will not electrically conduct.

Therefore, with a simple formation, the electric safety of the endoscope apparatus will be elevated. That is to say, even if the insertable section 2 of the endoscope 71 contacts the wiring of the electric system of the ignition plug or the like or the plus side of the battery apparatus 53, the endoscope 71 will not electrically conduct, therefore no spark will be generated and the endoscope apparatus, chassis 54, electric equipments, operator and observer will not be damaged. The other formations, operations and effects are the same as in the first embodiment.

Figure 6:
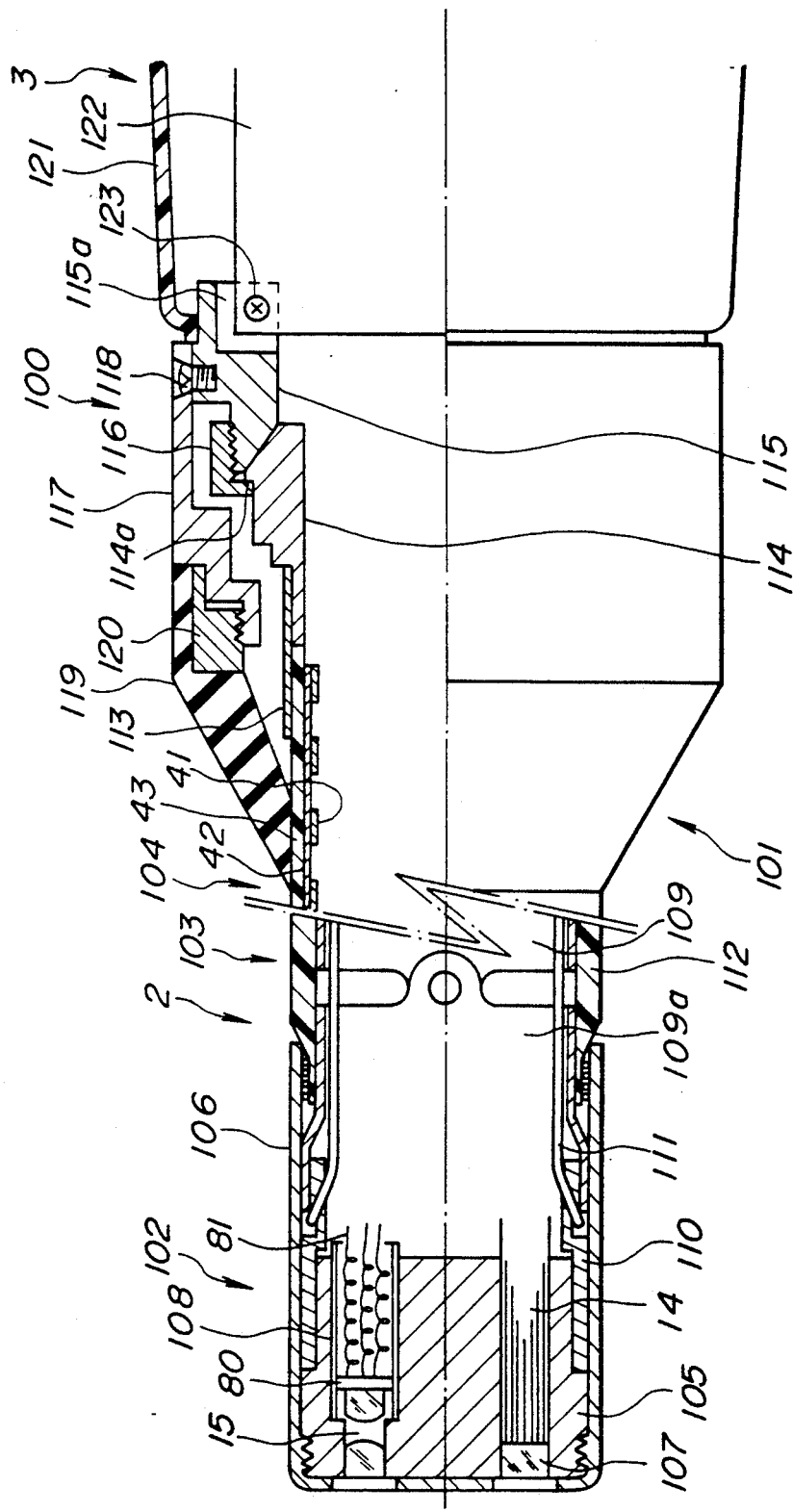
FIG. 6 is a sectioned view of an insertable section and operating section base part of an endoscope in the fourth embodiment of the present invention.

FIG. 6 shows the fourth embodiment of the present invention. In an endoscope 100 of this embodiment, the connecting member connecting the insertable section and operating section is formed of an electric insulative material.

The insertable section 2 of the endoscope 100 comprises a rigid tip part 102, a curvable part 103 and a soft part 104 in the order from the tip side. The above mentioned tip part 102 is provided with a tip part body 105 made of a metal. A cover 106 made of a metal is screwed on the outer periphery of this tip part body 105 provided on the tip surface with an illuminating window and observing window.

Inside the above mentioned illuminating window is arranged an illuminating lens 107 inside which is arranged the tip surface of the light guide 14. This light guide 14 is inserted through the insertable section 2, operating section 3 and universal cord not illustrate so that, when the illuminating light emitted from a light source apparatus not illustrated enters the entrance end, this illuminating light will be emitted from the above mentioned illuminating window.

Inside the above mentioned observing window is provided an objective optical system 15 in the image forming position of which is arranged a CCD 80. Signal wires 81 are extended from this CCD 80, pass through the flex 41 of the soft part 104 and are connected to an image processing apparatus not illustrated. The above mentioned CCD 80 and signal wires 81 are held in an insulating cylinder 108 made of plastics for the insulation from the tip part body 105.

By the way, in case a cylinder made of a metal is adopted to elevate the strength for holding the above mentioned insulating cylinder 108, the cylinder may be Teflon worked on the inside surface to secure the insulatability.

Also, the same as in the above described first embodiment, within the above mentioned curvable part 103 are provided a plurality of non electroconductive curvable rings 109 and the foremost curvable ring 109a is fixed to the above mentioned tip part body 105 through a ring 110 to which non electroconductive angle wires 111 are fixed and connected at the tips. The above mentioned curvable rings 109 are coated on the outer periphery with an electric insulative thick resin tube 112 which is engaged on the tip side with the above mentioned cover 106 on the inner peripheral surface side at the rear end.

On the other hand, the same as in the above described first embodiment, the above mentioned soft part 104 comprises a flex 41 made by spirally working a metal plate material, a metal blade 42 and an electric insulative resin tube 43 in the order from the inner peripheral side. The above mentioned soft part 104 enters at the rear end a protective part 101 covering and protecting the insertable section 2 base and is fixed to a mouthpiece 114 by a ring 113.

The above mentioned mouthpiece 114 is provided on the rear end side with a flange part 114a in contact with a connecting member 115 made of an electric insulative material plastics. The above mentioned connecting member 115 is provided on the outer periphery with a male screw part with which is screwed a female screw part of a joint member 116 engaging with the flange part 114a of the above mentioned mouthpiece 114 so that the above mentioned mouthpiece 114 and connecting member 115 may be securely fixed.

A cylindrical member 117 to which the flexing preventing part 101 is connected is fixed with a screw 118 on the outer peripheral surface of the above mentioned connecting member 115. A fixing metal piece 120 inserted into a rubber part 119 forming the essential part of the protective part 101 is screwed to the above mentioned cylindrical member 117 at the insertable section 2 side tip. The above mentioned rubber part 119 is made smaller in the outside diameter toward the insertable section 2 side so that the flexibility may gradually increase, the above mentioned resin tube 43 may be smoothly supported and the insertable section 2 may not flex or buckle.

The above mentioned cylindrical member 117 is engaged at the rear end with an operating section cover 121 made of hard plastics which is an electric insulative material. Within this operating section cover 121, a metallic base 122 holding the member forming the operating section 3 is fixed with a screw to the above mentioned operating section cover 121 on the eyepiece section side not illustrated and is fixed with a screw 123 to a plane part 115a of the above mentioned connecting member 115 on the insertable section 2 side.

In this embodiment, even if the metal part on the tip side of the insertable section 2 contacts the plus side of the battery apparatus 53, the electricity will be little likely to conduct to the endoscope insertable section 2 itself but, even if the insertable section 2 electrically conducted, the conduction would be interrupted by the connecting member 115 connecting the insertable section 2 and operating section 3, therefore the electric current would not flow through the light source apparatus and image processing apparatus. Thus, with a simple formation, the electric safety of the endoscope apparatus will be elevated.

Therefore, the same as in the above described respective embodiments, even if the metal part at the tip of the endoscope 100 touches the plus side of the battery apparatus 53, no electricity will conduct, no spark will be generated and no damage will be given to the endoscope apparatus and observer.

Figure 7:
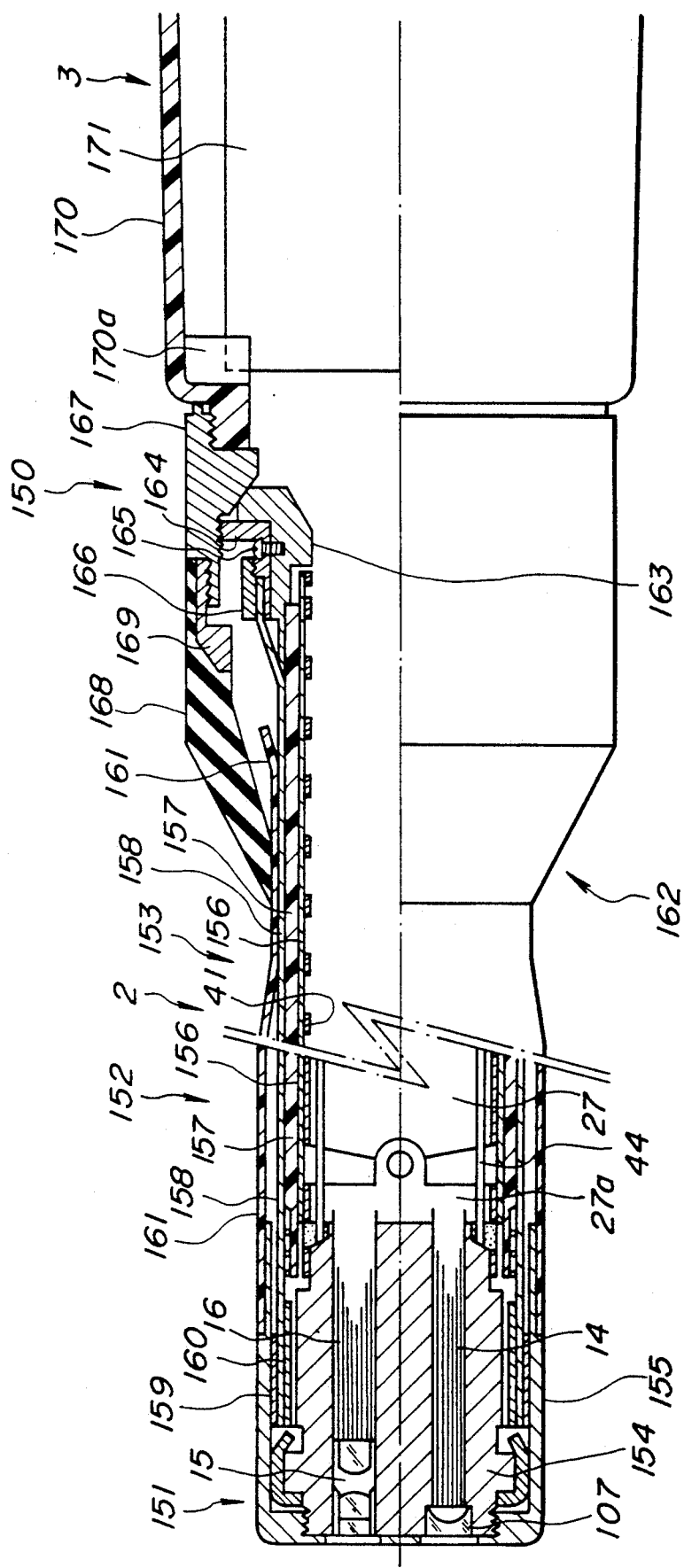
FIG. 7 is a sectioned view of an insertable section and operating section base part of an endoscope in the fifth embodiment of the present invention.

FIG. 7 shows the fifth embodiment of the present invention. In this embodiment, the connecting member 115 and cylindrical member 117 in the above described fourth embodiment are integrally formed of an electric insulative material.

The insertable section 2 of an endoscope 150 of this embodiment comprises a rigid tip part 151, a curvable part 152 and a soft part 153 in the order from the tip side.

The above mentioned tip part 151 is provided with a tip part body 154 made of a metal and a cover 155 made of a metal and screwed to the outer periphery of this tip part body 154. The above mentioned tip part body 154 is provided with an illuminating through hole and observing through hole parallel in the axial direction of the insertable section 2. Within the above mentioned illuminating through hole, an illuminating lens 107 is arranged and the tip surface of the light guide 14 is arranged and fixed inside this illuminating lens 107.

Within the above mentioned observing through hole, an objective optical system 15 is provided on the tip side and the image guide 16 is inserted and fixed on the tip side in the rear of this objective optical system 15. The tip surface of this image guide 16 is arranged in the image forming position of the above mentioned objective optical system 15.

Also, the same as in the above described first embodiment, the above mentioned curvable part 152 has a plurality of non electroconductive curvable rings 27 and the foremost curvable ring 27a is bonded and fixed to the above mentioned tip part body 154. The above mentioned curvable rings 27 are coated on the outer periphery with an inner blade net tube 156 made of a metal, electric insulative resin tube 157 and outer blade 158 made of a metal in the order mentioned.

The above mentioned inner blade 156 is fixed at the tip to the foremost curvable ring 27a and non electroconductive angle wires 44 are fixed at the tips to the inner periphery of the foremost curvable ring 27a with a non electroconductive bonding agent or the like.

The above mentioned outer blade 158 is fixed on the tip side to the inner peripheral surface of the above mentioned cover 155 with fixing rings 159 and 160 and an insulating tube 161 made, for example, of vinyl chloride is fitted to this cover 155 at the rear end, coats the curvable part 152 and soft part 153 and is extended into the protective part 162.

The soft part 153 is coated with the flex 41 made by spirally working a metal plate material, inner blade 156, resin tube 157 and outer blade 158 in the order from the inner peripheral side and the flex 41, inner blade 156 and resin tube 157 are fixed at the rear ends to a mouthpiece 163.

A ring 164 having a flange part is fitted to the above mentioned mouthpiece 163 on the outer periphery and is fixed with a screw 165 so as to fix the above mentioned outer blade 158 a held by these rings 164 and 166.

The above mentioned mouthpiece 163 is in contact at the rear end with a connecting member 167 made of an electric insulative material plastics and the male screw part of the flange part of the above mentioned ring 164 is screwed into the female screw part provided on the inner periphery of this connecting member 167 so that the above mentioned mouthpiece 163 and connecting member 167 may be securely fixed A fixing metal piece 169 inserted in a rubber part 168 forming an essential part of a flexing preventing part 162 is screwed to the above mentioned connecting member 167 at the tip on the side of the insertable section 2. The above mentioned rubber part 168 is made smaller in the outside diameter toward the insertable section 2 side so that the flexibility may gradually increase, the above mentioned insulating tube 161 may be smoothly supported as held between the above mentioned rubber part 168 and outer blade 158 and the insertable section 2 may not flex or buckle.

Thereby, the electric insulatability of the curvable part 152 and soft part 153 can be secured while retaining the mechanical strength and, in case the insulating tube 161 is broken, the above mentioned cover 155 will be removed and the insulating tube 161 will be able to be soon replaced.

Also, the above mentioned connecting member 167 is screwed at the rear end into an operating section cover 170 made of an electric insulative material hard plastics. Within this operating section cover 170, a base 171 holding a member forming the operating section 3 is fixed on the eyepiece part side not illustrated to the above mentioned operating section cover 170 with a screw and is held on the insertable section 2 side by a rib 170a provided within the above mentioned operating section cover 170.

In this embodiment, the metal part at the tip of the insertable section 2 and the operating section 3 are electrically perfectly insulated by the connecting member 150 and the same operations and effects as in the above described fourth embodiment are obtained.

Figure 8:
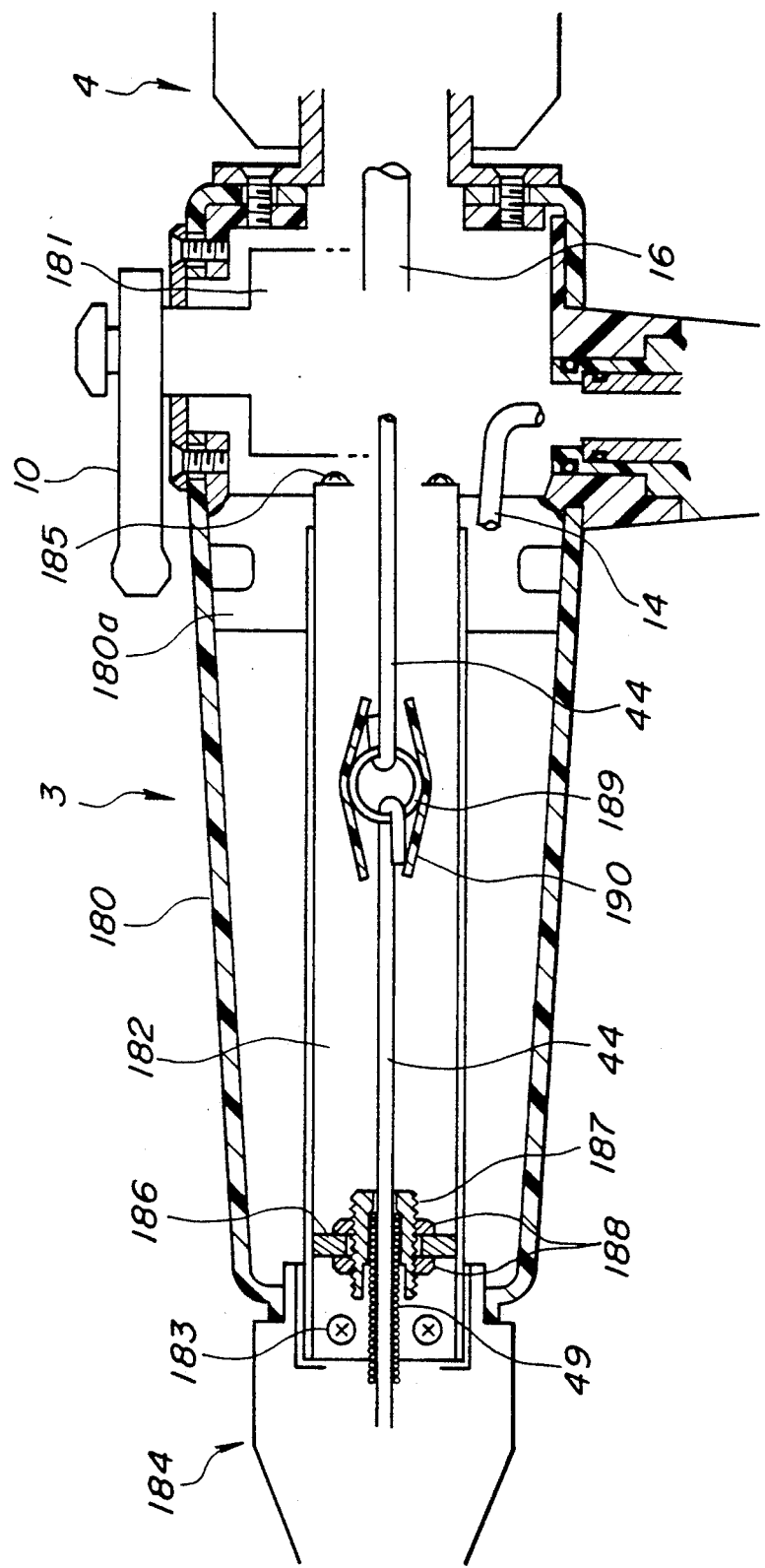
FIG. 8 is a sectioned view of an operating section of an endoscope in the sixth embodiment of the present invention.

FIG. 8 shows the sixth embodiment of the present invention. In this embodiment, an insulating member is interposed between the holding part of the operating section 3 of the endoscope 1 and the electroconductive member within the operating section 3.

The same as in the first embodiment, the image guide 16 and light guide 14 pass through the operating section 3. The image guide 16 is extended to the eyepiece section 4 and its rear end surface is opposed to an eyepiece optical system not illustrated within the eyepiece section 4. The light guide 14 is extended to a light guide connector not illustrated from the side of the operating section 3.

Within an operating section cover 180 formed of such electric insulative material as plastics, forming the outer surface of the above mentioned operating section 3 and used also as a holding part, a curving controlling mechanism 181 is housed on the eyepiece section 4 side. A curving operation knob 10 made of such electric insulative material as plastics and projecting out of the above mentioned operating section cover 180 is connected to this curving controlling mechanism 181.

Further, an angle wire 44 is connected to the above mentioned curving controlling mechanism 181 so that, when the doctor operates the above mentioned curving operation knob 10, the above mentioned angle wire 44 will be pulled to curve the insertable section 2 on the tip side.

A base 182 made of a metal and holding a member forming the operating section 3 is passed through the above mentioned operating section cover 180, is fixed at one end by screws 183 to a non electroconductive member 184 connected to a protective part and is fixed at the other end by screws 185 to a base supporting member 180a made of such non electroconductive material as plastics.

The above mentioned base 182 is folded back on the side ends to elevate the bending rigidity and has a plate 186 erected at one end on the insertable section 2 side, a hole is made in the rising part of this plate 186 and an adjusting screw 187 threaded on the outer periphery is inserted into this hole and is fixed by holding the above mentioned plate 188 with nuts 188.

The angle wire 44 made of a nylon coated stainless steel wire and extended out of the insertable section 2 is inserted through the above mentioned adjusting screw 187 and a coil pipe 49 protecting the above mentioned angle wire 44 is fitted at the end into the above mentioned adjusting screw 187 at one end on the insertable section 2 side so that the above mentioned angle wire 44 may be regulated in rocking.

After the adjustment of the curving angle of the insertable section 2 is completed, the angle wire 44 extended out of the insertable section 2 and inserted through the above mentioned adjusting screw 187 is connected with the angle wire 44 on the above mentioned curving controlling mechanism 181 side through a ring 189. The connecting part of the angle wires 44 by the above mentioned ring 189 is covered on the periphery with a protective tube 190 made of a thermoshrinking tube so as to be protected.

In this embodiment, even in case the electric insulatability of the insertable section 2 interior and angle wires 44 reduces, the angle wires 44 will be regulated in rocking by the plate 186 and therefore, even if the metal part on the tip side of the insertable section 2 contacts the plus side of the battery apparatus 53, the angle wires will not contact the other component members within the operating section 3 to electrically conduct.

In this case, if the above mentioned plate 186 is formed of such electric insulative material as plastics, the insulating effect will be higher. Even if the angle wire 44 reduced in the insulatability contacts the base 182, as the base 182 is also electrically insulated, no electricity will conduct to the outer surface of the operating section 3 which is a holding part and it will be safe.

That is to say, even if the metal part on the tip side of the insertable section 2 contacts the plus side of the battery apparatus 53 and the insertable section 2 electrically conducts, no electricity will conduct, therefore no spark will be generated and no damage will be given to the endoscope apparatus and observer.

Figure 9:
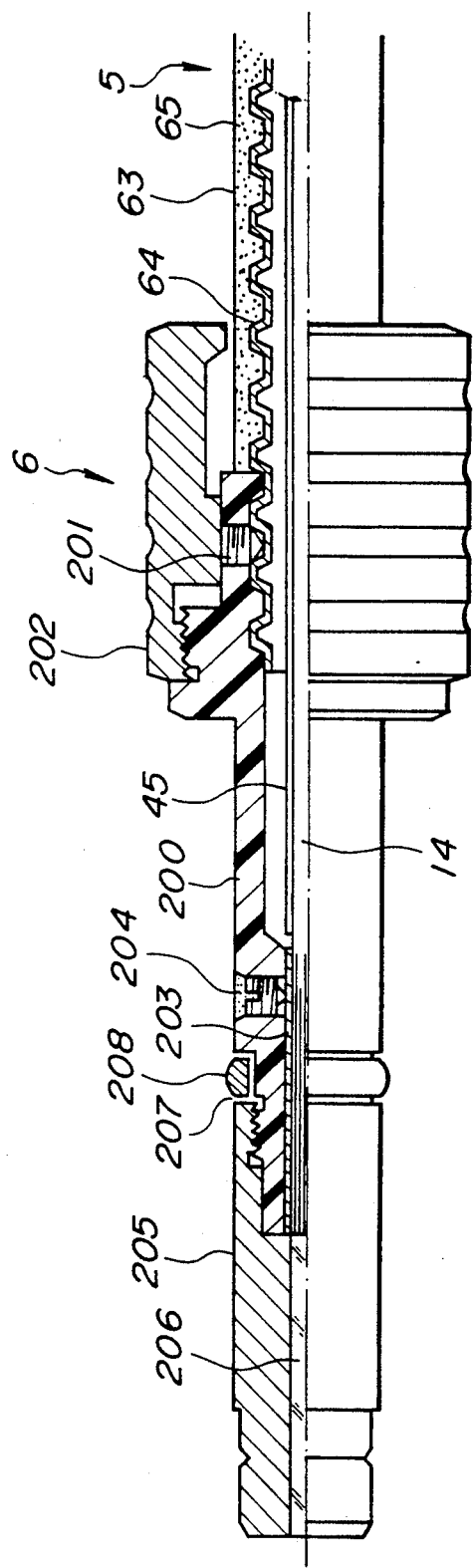
FIG. 9 is a sectioned view of a connector in the seventh embodiment of the present invention.

FIG. 9 shows the seventh embodiment of the present invention. In this embodiment, the light guide connector 6 of the endoscope connected to the light source apparatus is provided with an insulating member.

A flexible tube 63 forming a sheath of a light guide cable 5 connected to the light guide connector 6 of this embodiment is made by coating a flexible tube 64 made of a metal on the outer periphery with a protective tube 65 made of an insulative polyester resin or vinyl chloride resin. A light guide 14 coated with a protective tube 45 made of silicone is inserted through this flexible tube 63.

The above mentioned flexible tube 63 has the resin peeled off the tip part to expose the above mentioned tube 64 which is inserted into a connecting member 200 made of such electric insulative material as plastics and is fixed with a set screw 201.

A grip 202 is screwed onto the above mentioned connecting member 200 so as to cover and protect the above mentioned set screw 201 and to prevent the light guide cable 5 from bending.

The light guide 14 to which is bonded a mouthpiece 203 made of a metal is inserted at the tip into the axial center part of the above mentioned connecting member 200 and is fixed to the above mentioned connecting member 200 with a set screw 204.

A rod receptacle 205 made of a metal in consideration of the heat proofness is screwed onto the above mentioned connecting member 200 on the tip side. A rod lens 206 is bonded to the axial center part of this rod receptacle 205 and is fixed so as to be positioned on the tip side of the light guide 14 so that the above mentioned light guide 14 may be prevented by this rod lens 206 from being exposed directly to the heat of a light source not illustrated to reduce the performance.

Also, a groove 207 is formed on the outer surface of the connecting part of the above mentioned connecting member 200 and rod receptacle 205 and is fitted with an elastic ring 208 so that, in case the light guide connector 6 is inserted into a light source apparatus not illustrated, the above mentioned ring 208 will fit a recess on the light source apparatus side to securely connect the light guide connector 6.

In this embodiment, even if the metal part at the tip of the insertable section of the endoscope contacts the plus side of the battery apparatus 53 and the electricity is conducted to the light guide cable 101 by the metallic structural members within the endoscope insertable section and operating section, the conduction will be interrupted by the connecting member 200 of the light guide connector 6 and therefore no electric current will flow through the light source apparatus.

Therefore, with a simple formation, the safety of the endoscope apparatus will be elevated and, even if the endoscope apparatus contacts the plus side of the battery apparatus 53, no electricity will conduct, therefore no spark will be generated and no damage will be made to the endoscope apparatus and inspected object By the way, if the first embodiment is used together, the electric safety will be higher.

Figure 10:
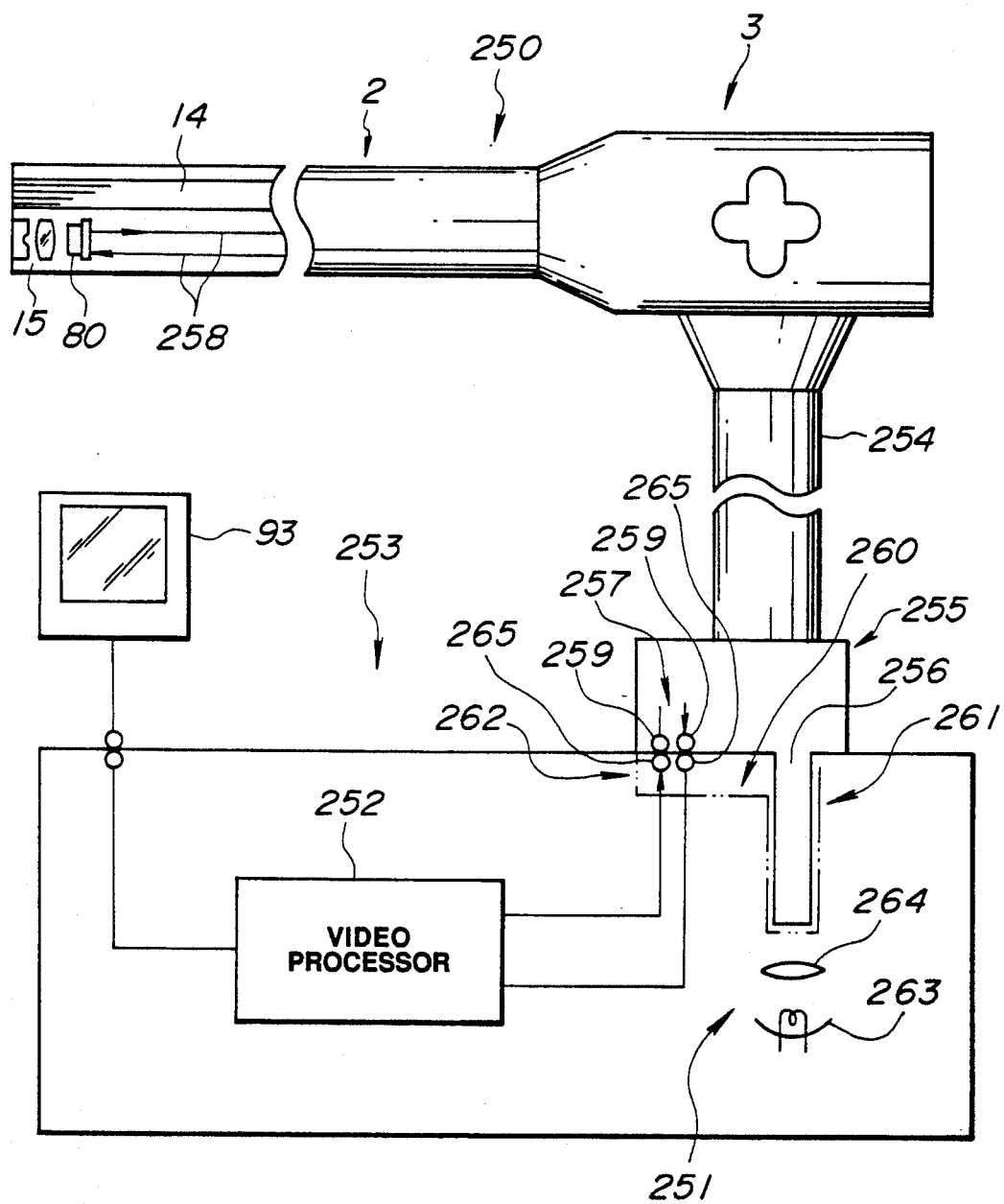
FIGS. 10 and 11 relate to the eighth embodiment of the present invention.
Figure 11:
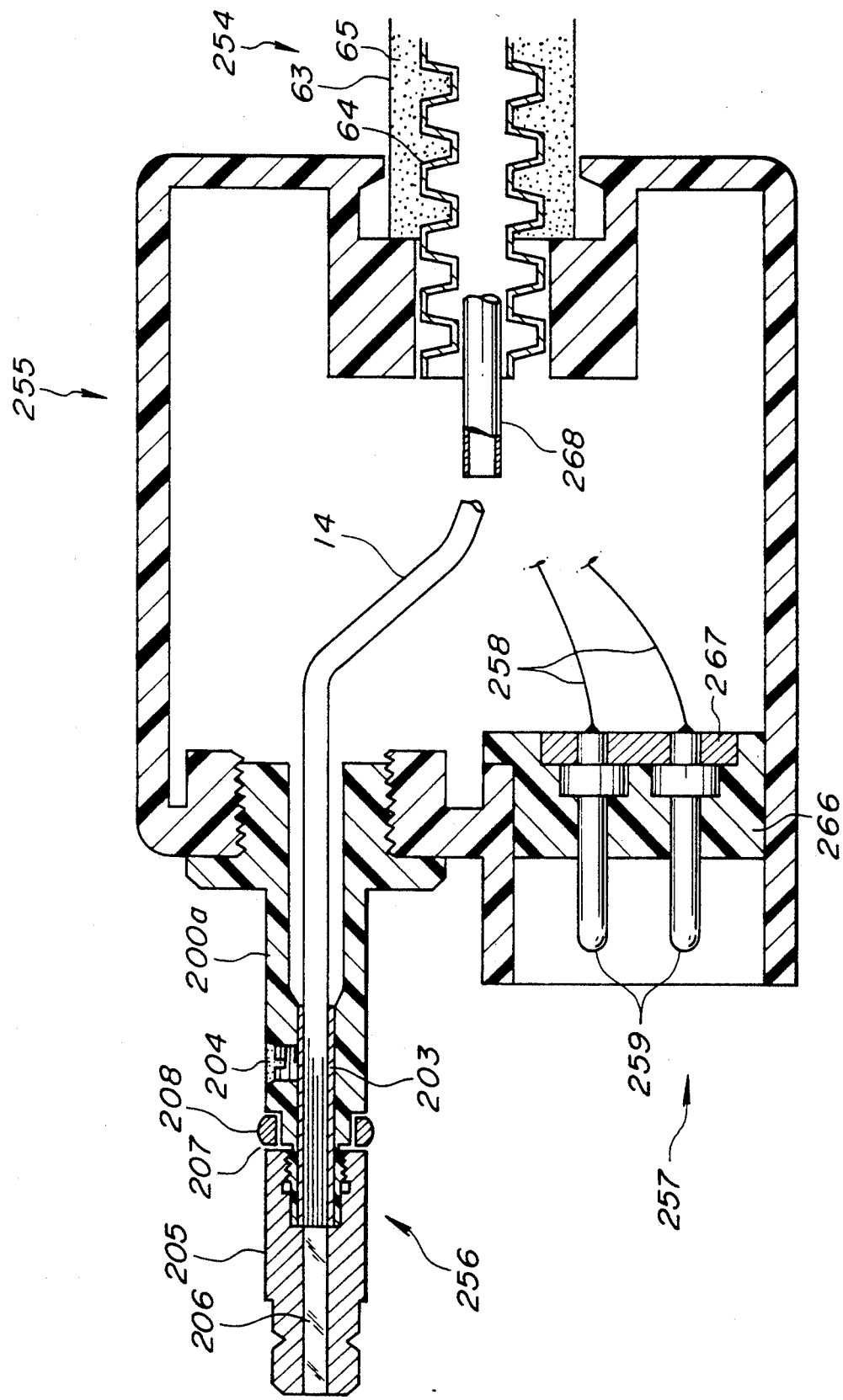

FIGS. 10 and 11 show the eighth embodiment of the present invention. In this embodiment, the connector for connecting the endoscope to the signal processing apparatus as an external apparatus is provided with an insulating member.

As shown in FIG. 10, an endoscope apparatus in this embodiment comprises an electronic endoscope 250 and a controlling unit 253 internally provided with a light source apparatus 251 and such signal processing apparatus as, for example, a video processor 252.

By the way, to the above mentioned controlling unit 253 can be connected an electronic endoscope and optical endoscope and can be connected not only the endoscopes 1, 71, 100 and 150 in the above described respective embodiments but also an optical endoscope fitted with an externally fitted television camera. The signal processing apparatus may be a curving motor controlling apparatus or the like.

Among these endoscopes, the endoscope 250 shown in FIG. 10 has the elongate insertable section 2 extended forward of the operating section 3 on the base side and has the universal cord 254 extended sidewise of this operating section 3 and provided at the tip with a connector 255.

At the tip of the above mentioned insertable section 2 is arranged the tip surface of the light guide 14 and is arranged an objective optical system 15. In the image forming position of this objective optical system 15 is internally provided a CCD 80.

The above mentioned light guide 14 and signal wires 258 of the CCD 80 are inserted through the insertable section 2, operating section 3 and universal cord 25 and are connected to the above mentioned connector 255.

The above mentioned connector 255 is provided with a light guide connecting part 256 and an electrode part 257. The above mentioned light guide 14 is connected at the entrance end to the above mentioned light guide connecting part 256. The signal wires 258 of the CCD 80 are connected to the terminals 259 of the above mentioned electrode part 257.

On the other hand, the above mentioned controlling unit 253 has a connector receptacle 260 connecting the above mentioned connector 255. This connector receptacle 260 is provided with a light guide receptacle 261 and a terminal receptacle 262. A light source apparatus 251 is internally provided in the rear of the above mentioned light guide receptacle 261.

The above mentioned light source apparatus 251 comprises a lamp 263 emitting an illuminating light and a condensing lens 264 leading the illuminating light from this lamp 263 to the light guide receptacle 261 and radiating it to the entrance end of the inserted and connected light guide 14 of the light guide connecting part 256.

The above mentioned video processor 252 is internally provided with a driver circuit for driving the above mentioned CCD 80 and a video signal processing circuit converting the signal from the above mentioned CCD 80 to a video signal and outputting it to the monitor 93 and the respective circuits are electrically connected to the contact 265 of the above mentioned terminal receptacle 262.

As shown in FIG. 11, the above mentioned connector 255 is connected with a universal cord 254 of the same formation as of the light guide cable 5 in the above described seventh embodiment, has a light guide connecting part 256 having a connecting member 200a of a somewhat modified form of the connecting member 200 of the light guide connector 6 of the above described seventh embodiment and has an electrode part 257. The above mentioned connecting member 200a is made of plastics which is an electric insulative material.

In the above mentioned electrode part 257, terminals 259 are fitted in a connection member 266 made of such electric insulative material as, for example, engineering plastics and having a plurality of holes and are fixed at the rear end with a pressing plate 267 made also of such electric insulative material so as not to be pulled out.

Signal wires 258 are connected to the above mentioned terminals 259, are coated together with the light guide 14 from the above mentioned light guide connecting part 256 with a protective tube 268 made of silicone, are inserted through the universal cord 254 and are connected to the CCD 80 at the tip of the insertable section 2.

In the endoscope 250 provided with the connector 255 of the above formation, even if the metal part at the tip of the insertable section 2 contacts the plus side of the battery apparatus 53 and the electric current is conducted to the universal cord 254 by the metallic structural members within the insertable section 2 and operating section 3, the conduction will be interrupted by the connecting members 266 and 200 of the connector 255 and therefore the electric current will not flow through the light source apparatus 251 and video processor 252.

Therefore, with a simple formation, the safety of the endoscope apparatus will be elevated and, even if the endoscope apparatus contacts the plus side of the battery apparatus 53 connected to the inspected object, no electricity will be conducted, therefore no spark will be generated and the endoscope apparatus and inspected object will not be damaged. By the way, if the first embodiment is used together, the electric safety will be higher.

FIGS. 12 to 15 show the ninth embodiment of the present invention. This embodiment is of an endoscope in which the light source apparatus is fitted directly to the operating section to improve the workability on the spot.

Figure 12:
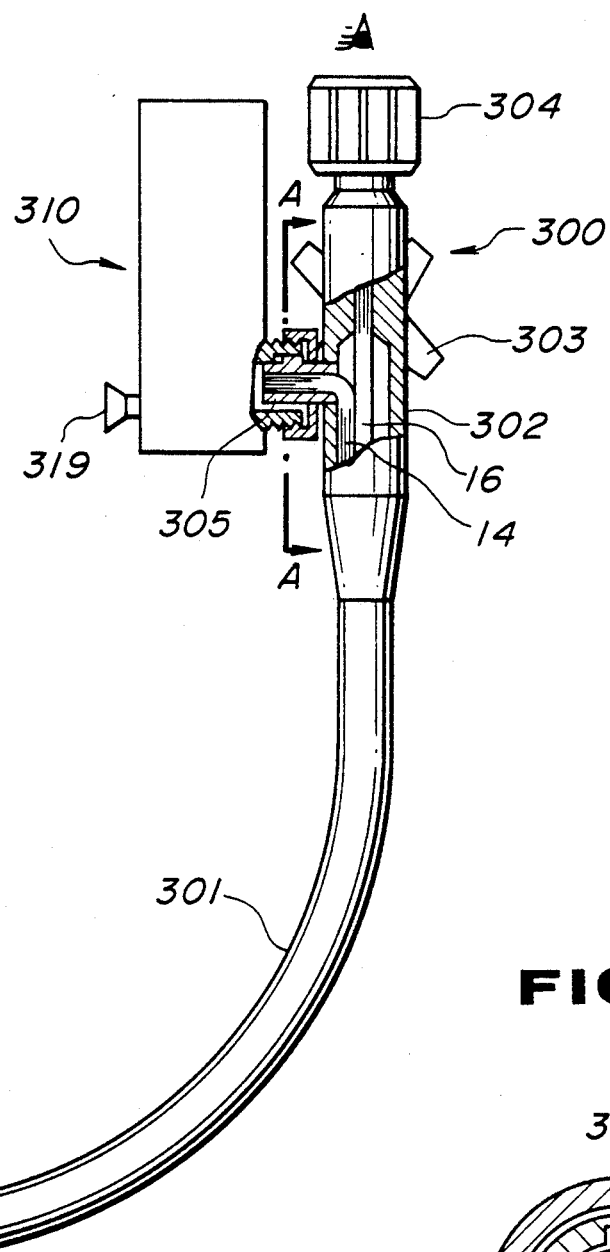
FIGS. 12 to 15 relate t the ninth embodiment of the present invention.
Figure 13:
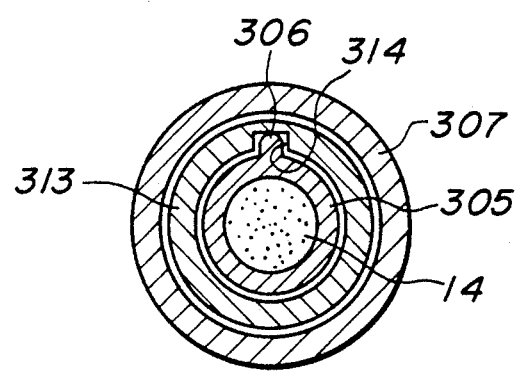

As shown in FIG. 12, an endoscope 300 of this endoscope comprises an elongate insertable section 301, an operating section 302 provided at the rear end of this insertable section 301 and used also as a holding part and an eyepiece section 304 provided at the rear end of this operating section 302.

The above mentioned insertable section 301 is formed of a metal to secure the strength on the outer periphery of the tip part and is coated with a resin tube so as to be electrically insulated in the rear of this metal part. The tip surfaces of the light guide 14 and image guide 16 are arranged within the tip part of the above mentioned insertable section 301. The above mentioned image guide 16 is inserted through the above mentioned insertable section 301 and operating section 302 and the rear end surface is opposed to an eyepiece optical system not illustrated of the above mentioned eyepiece section 304.

The above mentioned operating section 302 is made of such electric insulative material as hard plastics on the outer surface to be a holding part and is provided on the side with a curving operation knob 303 made of such electric insulative material as plastics so that, when this curving operation knob 303 is operated, the above mentioned insertable section 301 will be curved at the tip.

Further, the above mentioned operating section 302 is provided on the side with a standing cylindrical mouthpiece 305 for fitting a light source apparatus 310. This mouthpiece 305 is provided to stand on the outer surface of the above mentioned operating section 302 so as not to contact the metal part within the above mentioned operating section 302. The above mentioned light guide 14 inserted through the above mentioned insertable section 301 and extended sidewise from the above mentioned operating section 302 is inserted through this standing mouthpiece 305 so as to be exposed at the end.

By the way, the above mentioned mouthpiece 305 may be formed of such electric insulative material as engineering plastics.

Figure 14:
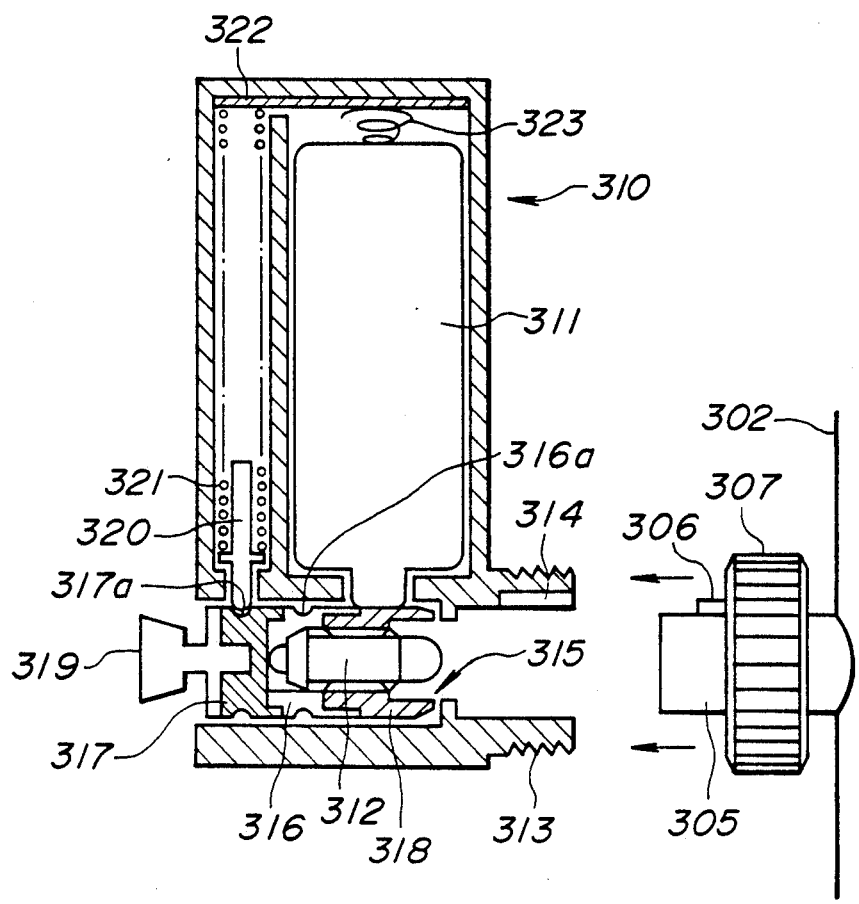

On the other hand, as shown in FIG. 14, the above mentioned light source apparatus 310 is provided within with a battery 311 and illuminating lamp 312 and is formed to be like a long rectangular paralelepiped in the lengthwise direction of the above mentioned battery 311.

Further, a cylindrical connecting part 313 fitted and engaged with the above mentioned mouthpiece 305 on the outer periphery is projected on the side at one end in the lengthwise direction of this light source apparatus 310.

The above mentioned connecting part 313 is threaded on the outer periphery so that a fixing nut 307 fitted to the above mentioned mouthpiece 305 may be screwed to the connecting part 311 when the above mentioned connecting part 313 is fitted to the above mentioned mouthpiece 305. A projection 306 is provided on the outer periphery of the above mentioned mouthpiece 305. A long groove 314 is formed in the axial direction on the inside surface of the above mentioned connecting part 313 as opposed to this projection 306 so that, only when the projection 306 fits in the long groove 314, the connecting part 313 will be able to fit the mouthpiece 305 and the illuminating light from the light source apparatus 310 will be able to be led to the tip of the above mentioned insertable section 301 through the light guide 14.

Also, the above mentioned light source apparatus 310 is removably fitted below the above mentioned battery 311 with a lamp holder 315 holding the above mentioned illuminating lamp 312. This lamp holder 315 is provided outside with a switch contact member 317 and inside with a cylindrical battery contact member 318 with an insulating tube 316 interposed between them.

Figure 15:
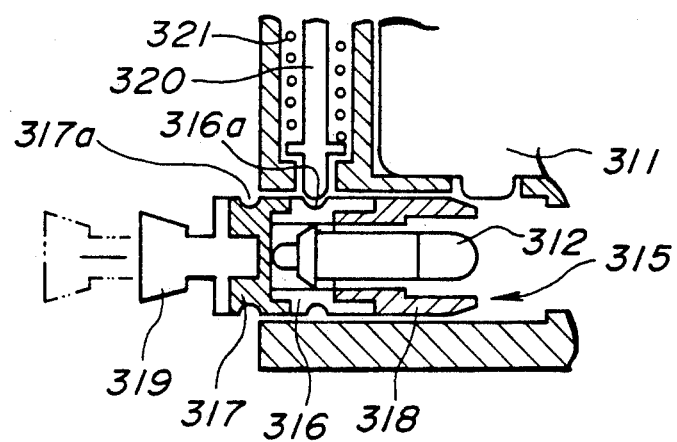

The above mentioned switch contact member 317 is provided with an outward projecting grip 319 so that, at the time of lighting as shown in FIG. 14, the switch contact member 317 may contact a switch pin 320. As shown in FIG. 15, when the grip 319 is pulled to slightly displace the lamp holder 315, the battery contact member 318 will separate from the terminal of the battery 311 and the switch pin 320 will contact the insulating tube 316.

Further, the above mentioned switch pin 320 energizes the above mentioned lamp holder 315 with an electroconductive spring 321 so as to fit in an engaging groove 317a formed on the outer periphery of the switch contact member 317 when the light is on and to fit in another engaging groove 316a formed on the outer periphery of the insulating tube 316 when the light is off.

By the way, the above mentioned switch pin 320 is electrically connected with the electroconductive spring 321 and is electrically connected to the other terminal of the battery 311 through a contact plate 322 and contact spring 323.

In the endoscope 300 fitted integrally with such light source apparatus 310, even if the metal part on the tip side of the insertable section 301 contacts the plus side of the battery apparatus 53 and the electricity is conducted even into the operating section 302 by the component members made of a metal within the insertable section 301 and operating section 302, as the operating section 302 which is a holding part is made on the outer surface of such electric insulative material as hard plastics, no electric shock will be given to the observer. As the mouthpiece 305 is electrically insulated and the light guide 14 is of an electric insulative material, no electricity will be conducted to the light source apparatus 310 fitted to the outer surface of the operating section 302 which is a holding part.

Therefore, with a simple formation, the electric safety of the endoscope apparatus will be elevated. That is to say, even if the insertable section 301 of the endoscope 300 contacts the plus side of the battery apparatus 53, no electricity will conduct through the endoscope 300, therefore no spark will be generated and the endoscope apparatus, operator and observer will not be damaged.

By the way, the present invention is not limited to the above mentioned respective embodiments. For example, an insulating part may be provided in the course of the part coated with a electric insulative member in the insertable section. Also, the whole operating section may be formed of an electric insulative material so as to be insulated between the insertable section and the light guide cable or universal cord.

It is apparent that, in this invention, different working modes can be formed in a wide range on the basis of this invention without deviating from the spirit and scope of the invention. This invention is not restricted by specific working modes except being limited by the appended claims.

What is claimed is:

1. An endoscope having an operating section and an electrically isolated insertable section which is to be inserted into an object to be inspected, comprising:
    an operating section;
    an insertable section connected to said operating section, said insertable section having at least one portion in which an electroconductive member is exposed, said insertable section being electrically isolated from said operating section;
    said insertable section including an insulating member disposed in a path between said electroconductive member and said operating section for electrically insulating said electroconductive member and said operating section.

2. An endoscope according to claim 1, wherein said electroconductive member has a tip part, an outer blade, and a flex.

3. An endoscope according to claim 1, wherein said insertable section to be inserted into the inspected object has a curvable part connected to said tip part.

4. An endoscope according to claim 3 wherein said insertable section further comprises a flexible part connected to a rear portion of said curvable part, and comprising said insulating member interposed between said curvable part and said soft part.

5. An endoscope according to claim 3 further comprising a plurality of angle wires which are connected to said curvable part, said angle wires being selectively actuatable to cause curving of said curvable part, and said angle wires being covered with a non-electroconductive member.

6. An endoscope according to claim 3, wherein said plurality of angle wires are formed of non-electroconductive members, said angle wires being selectively actuatable to cause curving of said curvable part, and said angle wires being covered with a non-electroconductive member.

7. An endoscope according to claim 3, wherein said insertable portion includes a curvable part, said curvable part including a plurality of rings in which adjacent pairs of said plurality of rings are pivotably connected, and said curvable part carrying a plurality of angle wires connected to said insertable section for causing pivoting of said rings to curve said curvable part, and wherein said rings and said plurality of angle wires are connected through non-electroconductive members.

8. An endoscope according to claim 7, wherein at least a part of said rings are formed of non-electroconductive members.

9. An endoscope having an operating section and an electrically isolated insertable section which is to be inserted into an object to be inspected, comprising:
    an operating section also serving as a holding part;
    an insertable section connected to said operating section, said insertable section having at least one portion in which an electroconductive member is exposed, said insertable section being electrically isolated from said operating section;
    said operating section being connected to a connecting cable which connects said holding part to an external apparatus, said operating section being disposed at a rear end of said insertable section;

said insertable section including an insulating member electrically insulating said electrically conductive portion of said insertable section and said operating section, said insulating member being disposed between ends connecting said electroconductive portion to an outer apparatus of said connecting cable.

10. An endoscope according to claim 1 or 9 wherein said insertable section is formed of an electroconductive tip part and a flexible part connected to said tip part, and comprising an insulating member which is interposed between said tip part and said soft part.

11. An endoscope according to claim 9, wherein said insulating member is provided in connecting portion which connects said insertable section and said operating section.

12. An endoscope according to claim 9, further comprising an insulating member which is interposed between said holding part and an electrically conductive portion within said operating section.

13. An endoscope according to claim 9 wherein said insulating member is provided in a connecting part of said operating section and said connecting cable.

14. An endoscope according to claim 9 wherein a light source apparatus as an outer apparatus is connected to said operating section through said connecting cable and an insulating member electrically insulating an electroconductive member included in a sheath of a connector disposed at an end of said connecting cable is provided in said connector.

15. An endoscope according to claim 9 wherein a signal processing apparatus as an outer apparatus is connected to said operating section through said connecting cable, and an insulating member electrically insulating an electroconductive member included in a sheath of a connector disposed at an end of said connecting cable is provided in said connector.

16. An endoscope according to claim 9 further comprising an eyepiece section connected to a rear of said operating section, whereby an optical image of the inspected object can be observed.

17. An endoscope according to any one of claims 1, 3 or 9 wherein an imaging device for imaging an inspected object is arranged in a tip part of the insertable section.

18. An endoscope having an operating section and an electrically isolated insertable section which is to be inserted into an object to be inspected, comprising:

an operating section;

an insertable section connected to said operating section, said insertable section having at least one portion in which an electroconductive member is exposed, said insertable section being electrically isolated from said operating section; and a light source apparatus which is fitted directly to a holding part serving as said operating section, wherein, in a path leading from said electroconductive member to said holding part, an insulating member electrically insulating said electrically conductive portion and said holding part is provided.

* * * * *